(12) United States Patent
Hortobágyi et al.

(10) Patent No.: US 11,008,594 B2
(45) Date of Patent: May 18, 2021

(54) PROCESS FOR THE PREPARATION OF TRIPLE-BOND-CONTAINING OPTICALLY ACTIVE CARBOXYLIC ACIDS, CARBOXYLATE SALTS AND CARBOXYLIC ACID DERIVATIVES

(71) Applicant: CHINOIN GYÓGYSZER ÉS VEGYÉSZETI TERMÉKEK GYÁRA ZRT., Budapest (HU)

(72) Inventors: Irén Hortobágyi, Budapest (HU); István Lászlófi, Budapest (HU); Zsuzsanna Kardos, Budapest (HU); József Molnár, Budapest (HU); László Takács, Budapest (HU); Tamás Bán, Budapest (HU)

(73) Assignee: CHINOIN PHARMACEUTICAL AND CHEMICAL WORKS PRIVATE COMPANY LTD., Budapest (HU)

( * ) Notice: Subject to any disclaimer, the term of this patent is extended or adjusted under 35 U.S.C. 154(b) by 187 days.

(21) Appl. No.: 16/087,402

(22) PCT Filed: Mar. 21, 2017

(86) PCT No.: PCT/EP2017/056689
§ 371 (c)(1),
(2) Date: Sep. 21, 2018

(87) PCT Pub. No.: WO2017/162667
PCT Pub. Date: Sep. 28, 2017

(65) Prior Publication Data
US 2020/0123578 A1    Apr. 23, 2020

(30) Foreign Application Priority Data

Mar. 22, 2016   (HU) .................................. P1600204

(51) Int. Cl.
| | |
|---|---|
| *C12P 7/62* | (2006.01) |
| *C07F 9/40* | (2006.01) |
| *C12P 7/40* | (2006.01) |
| *C12P 41/00* | (2006.01) |
| *C07C 57/18* | (2006.01) |
| *C07C 69/24* | (2006.01) |

(52) U.S. Cl.
CPC .............. *C12P 7/62* (2013.01); *C07F 9/4015* (2013.01); *C12P 7/40* (2013.01); *C12P 41/005* (2013.01); *C07C 57/18* (2013.01); *C07C 69/24* (2013.01)

(58) Field of Classification Search
CPC .. C12P 7/62; C12P 7/40; C12P 41/005; C07F 9/4015; C07C 57/18; C07C 69/24; C07C 51/09; C07C 69/606; C07B 41/12; C07B 57/00; C07B 41/08; C07B 53/00
See application file for complete search history.

(56) References Cited

U.S. PATENT DOCUMENTS

2014/0275266 A1    9/2014  Wang et al.

FOREIGN PATENT DOCUMENTS

| EP | 0233656 A1 | 8/1987 |
| JP | 5-84094 A | 4/1993 |
| JP | 2001-31625 A | 2/2001 |
| WO | WO 93/25704 A1 | 12/1993 |
| WO | WO 2014/144500 A2 | 9/2014 |

OTHER PUBLICATIONS

Carvalho et al., International Journal of Molecular Sciences, 2015, vol. 16, p. 29682-29716.*
Bornscheuer et al., "Hydrolases in Organic Synthesis. Regio- and Stereoselective Biotransformations, Lipases and Esterases," Hydrolases in Organic Synthesis: Regio- and Stereoselective Biotransformations, XP002538624, Nov. 2005, pp. 61-183.
Hungarian Search Report for Hungarian Application No. P1600204, dated Oct. 5, 2016, with English translation.
International Search Report (Form PCT/ISA/210) for International Application No. PCT/EP2017/056689, dated Jun. 26, 2017.
Wakita et al., "Preparative resolution of 2-methyl-4-hexynic acid for the synthesis of optically active m-phenylene PGI$_2$ derivatives and determination of their absolute configuration," Tetrahedron: Asymmetry, 2000, pp. 2981-2989.
Written Opinion of the International Searching Authority (Form PCT/ISA/237) for International Application No. PCT/EP2017/056689, dated Jun. 26, 2017.

* cited by examiner

*Primary Examiner* — Kade Ariani
(74) *Attorney, Agent, or Firm* — Birch, Stewart, Kolasch & Birch, LLP

(57) ABSTRACT

The invention provides a new enzimatic process for the preparation of chiral carboxylic acids, their salts and acid derivatives of the general formula (I) by enzymatic hydrolysis of racemic carboxylic acid ester of the general formula (II) and optionally subsequent esterification or acylation.

20 Claims, No Drawings

PROCESS FOR THE PREPARATION OF TRIPLE-BOND-CONTAINING OPTICALLY ACTIVE CARBOXYLIC ACIDS, CARBOXYLATE SALTS AND CARBOXYLIC ACID DERIVATIVES

The subject of our invention is process for the preparation of

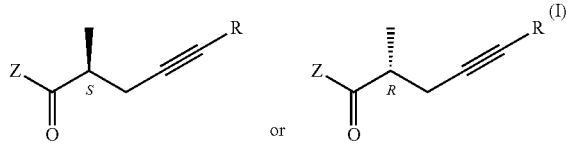

triple-bond-containing optically active carboxylic acids, salts, esters, phophonates of the general formula I,
where in the formulae
R=H or methyl group
Z=OH, OM, OR' or $CH_2$—$P(O)(OY)_2$-group, wherein
  M=metal ion, protonated ammonia or amine,
  R'=Me, Et, Pr, i-Pr, Bu, and
  Y=Me or Et.

During the process the racemic carboxylic acid esters are transformed into the optically active carboxylic acids by enzymatic hydrolysis. From the optically active carboxylic acids the optically active esters are prepared. The optically active esters are then converted into optically active phosphonates. The optically active phosphonates may be utilized for construction of the side-chain of optically active modified prostaglandins, prostacyclins and carbacyclins (e.g. Beraprost, Iloprost, 3-oxa-Iloprost, Icaprost, Cicaprost, Isocicaprost) difluoro-prostacyclins.

The optically active carboxylic acids may also be used as building blocks in the synthesis of Cruentaren A, the macrolide exerting antifungal and cytostatic effects.

According to the state of the art, the optically active carboxylic acids and carboxylic acid derivatives relating to the invention are prepared by lengthy chiral syntheses, requiring expensive and/or poisonous reagents, as demonstrated by the following examples:

1. From racemic acids via salt formation with chiral amines (H. Wakita, H. Yoshiwara, Y. Kitano, H. Nishiyama, H. Nagase, H; *Tetrahedron: Asymmetry*, 2000, 11(14), 2981-2989; JP 2001031625)

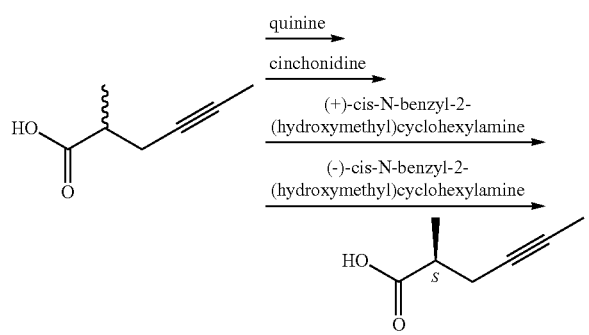

The Japanese researchers resolved the 2-methyl-4-hexynoic acid.

Drawbacks of the known method are the use of costly chiral amines and low stereoselectivity. Applying N-benzylamine derivative the yield (calculated for 50% racemic product) was 18.4 and 29.8%, and the enantiomeric excess was also very low, 20.8 and 13.6%.

The (R)-configuration acid displaying 99.9% enantiomeric purity was obtained after 10 recrystallizations of the salt formed with quinine.

The (S)-configuration acid displaying 99.6% enantiomeric purity was obtained following 9 recrystallizations of the salt formed with cinchonidine.

2. From racemic acids by formation of diastereomeric amides with chiral amines. (W. Skuballa, E. Schillinger, C. S. Stürzebecher, H. Vorbrüggen; *J. Med. Chem.*, 1986, 29, 315-317.)

2-Methyl-4-heptynoic acid was transformed into the acid chloride by treatment with phosphorus trichloride, from the acid chloride the diastereomeric amides were prepared with (−)-phenylglycinol, the diastereomers were separated by chromatographic method and hydrolyzed in acidic dioxane. The absolute configuration of the optically active acids was determined after saturation of the triple-bond by comparing the obtained methylheptanoic acids with the 2-methyl-alkanoic acids of known absolute configuration.

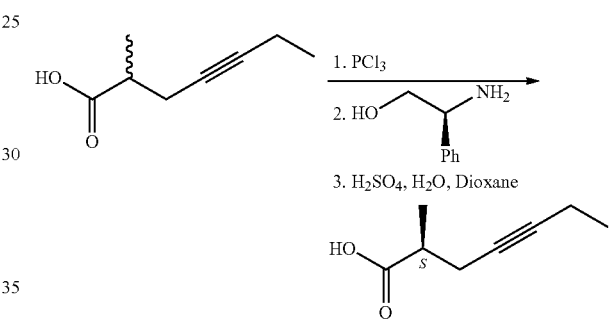

The optically active acid on treatment with diazomethane gave the methyl ester, which then was transformed with diethyl methyl phosphonate into the optically active phosphonate. Drawback of the method is the use of environmentally harmful phosphorus trichloride.

3. In patent application US 2014/02755266 A1, too, phenylglycinol enantiomers were used for the preparation of the 2-methyl-4-heptynoic acid enantiomers.

4. Transformation of chiral 2-methyl-carboxylic acid via triple-bond formation (E. J. Corey, Ch. J. Helal; *Tetrahedron Letters*, 1997, 38(43), 7511-7514.).

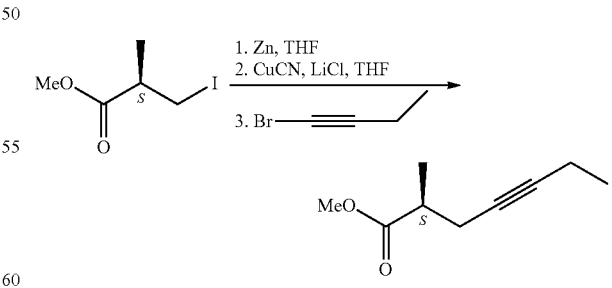

According to the method the chiral 3-hydroxy-2-methyl-propionic acid methyl ester was converted in two steps in 87% yield into the iodo-derivative, which was further transformed to give in 60% yield the desired triple-bond-containing derivative, the 2-methyl-4-heptynoic acid methyl ester.

5. Asymmetric synthesis by use of chiral iron-complex (G. J. Bodwell, S. G. Davies; *Tetrahedron: Asymmetry*, 1991, 2(10), 1075-1082.)

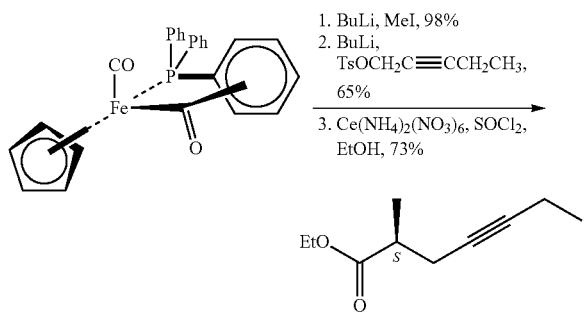

The chiral auxiliary material was alkylated first with methyl-, then with pent-2-ynyl-group, the auxiliary material was removed by oxidation with cerium ammonium nitrate. The chiral acid was transformed into the ethyl ester.

Disadvantage of the method is the use of expensive and poisonous iron-complex.

6. Asymmetric synthesis using chiral oxazolidine derivative

Chiral oxazolidine was first applied by J. Westerman and his co-workers (M. Harre, J. Trabandt, J. Westermann; *Liebigs Ann. Chem.*, 1989, 1081-1083.) for the preparation of triple-bond-containing chiral acid derivatives.

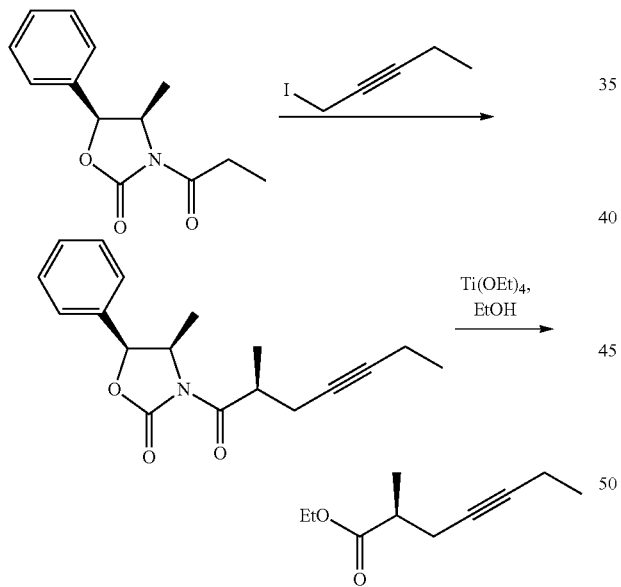

4-Methyl-5-phenyl-oxazolidinone was reacted with iodobutyne derivative, the chiral auxiliary group was then cleaved by boiling with titanium ethylate. From the resulting ethyl ester the phosphonate was prepared.

Disadvantage of the method is the relatively low yield (62%) and poor optical purity (de=80%).

7. Vermeeren and his co-workers prepared the optically active 2-methyl-4-heptynoic acid ethyl ester (R=Et) (M. Lerm, H-J. Gais, K. Cheng, C. Vermeeren; *J. Am. Chem. Soc.*, 2003, 125(32), 9653-9667.) and also the optically active 2-methyl-4-hexynoic acid ethyl ester (R=Me) (G. J. Kramp, M. Kim, H-J. Gais, C. Vermeeren; *J. Am. Chem. Soc.*, 2005, 127(50), 17910-17920.). The authors used benzyl-substituted oxazolidine as chiral auxiliary material.

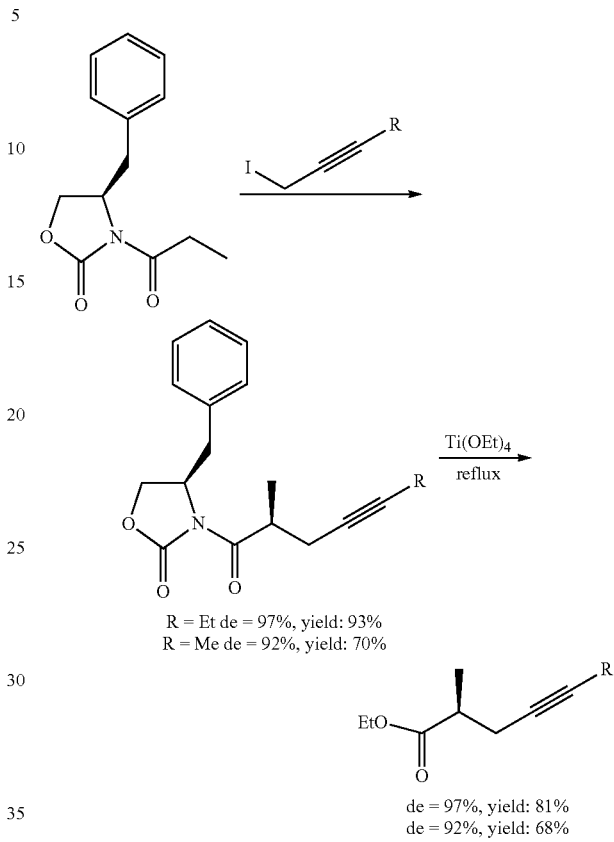

Using this method the yield and also the enantiomeric purity increased significantly, disadvantages of the method are, however, difficult scale-up, use of extreme reaction conditions and titanium ethylate.

By the above method was prepared the 2-methyl-4-hexynoic acid ethyl ester for the synthesis of Cruentaren A (A. Fürstner, M. Bindl, L. Jean; *Angew. Chem. Int. Ed.*, 2007, 46(48), 9275-9278; M. Bindl, L. Jean, J. Hermann, R. Müller, A. Fürstner, *Eur. J.*, 2009, 15(45), 12310-12319.).

8. In patent application WO 2012174407 A1, too, benzyloxazolidine is applied for the preparation of the optically active 2-methyl-4-hexynoic acid ethyl ester, and in patent application US 20140275266 A1 for the preparation of the optically active 2-methyl-4-hexynoic acid methyl ester, as well as in patent applications WO 2014015246 A1, WO 2014015247 A1, WO 2015009991 A2 for the preparation of optically active 2-methyl-4-hexynoic acid, optically active 2-methyl-4-heptynoic acid and their esters.

9. As disclosed in patent application WO 2015179427 A1, pseudoephedrine enantiomers may also be used as chiral auxiliary materials for the preparation of optically active 2-methyl-4-hexynoic acid and its derivatives.

According to the method of the present application, we prepare the chiral carboxylic acids, carboxylate salts and carboxylic acid derivatives by enzymatic hydrolysis of the racemic carboxylic acid esters.

The enzymatic hydrolysis proceeds under mild reaction conditions at room temperature, at almost neutral pH. Due to the mild reaction conditions the process may also be applied in the case of chemically sensitive carboxylic acid esters, and because of the low energy need, the process is environment friendly.

The optically active phosphonates prepared by the process according to the invention may be utilized in the synthesis of optically active modified prostaglandin, prostacyclin and/or carbacyclin derivatives.

According to the above, the subject of our invention is a process for the preparation of chiral carboxylic acids, carboxylate salts and carboxylic acid derivatives of the general formula I.

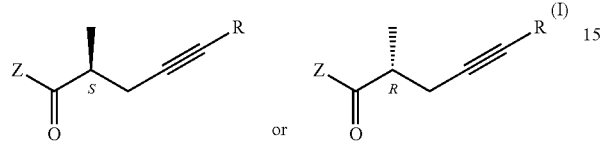

where in the formulae
R=H or methyl group
Z=OH, OM, OR' or P(O)(OY)$_2$ group, wherein
  M=metal ion, protonated ammonia or amine
  R'=Me, Et, Pr, i-Pr, Bu, and
  Y=Me or Et,
in a way that a racemic carboxylic acid ester of the general formula II.

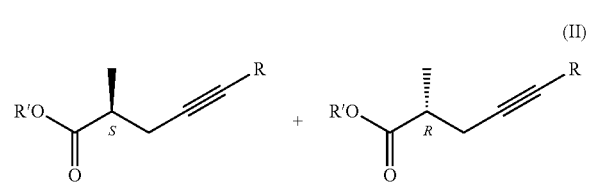

where the meanings of Z=OR' and R' are as defined above, is enzymatically hydrolyzed, if desired, for the preparation of compounds of the general formula I. wherein Z means OR' group the obtained compound of the general formula I. wherein Z stands for OH group is esterified, if desired, for the preparation of a compound of the general formula I. wherein Z stands for P(O)(OY)$_2$-group the resulting ester is acylated, and if desired the obtained compound of the general formula I. is transformed into its salt or liberated from its salt.

In the course of the hydrolysis as solvent, ethers, hydrocarbon-type and aromatic solvents, such as diisopropyl ether, methyl tert.-butyl ether, n-hexane, toluene may be applied. According to a favoured embodiment of the invention, methyl tert.-butyl ether is applied as solvent for the hydrolysis.

Depending on the amount and activity of the enzyme, the reaction time is 2-48 hours. Temperature of the reaction is 20-40° C.

Enzymatic catalysis is present in almost all fields of organic chemistry where the transformation is highly stereoselective, or where mild reaction conditions are needed because of the sensitivity of the intermediates. The most widely used enzymes are the inexpensive and commercially readily available hydrolases, among them esterases, e.g. lipases, such as AZ lipase (*Candida rugosa*), AK lipase (*Pseudomonas fluorescens*), CAL-A (*Candida antarctica* A), CAL-B (*Candida antarctica* B), PS lipase (*Burkholderia cepacia*), *Rhizopus arrhizus* lipase, *Rhizomucor miehei* lipase, *Pseudomonas cepacia* lipase, pig pancrease lipase (PPL), *Candida rugosa* lipase (CR), *Pseudomonas fluorescens* lipase (PF), *Aspergillus niger* lipase (AN), calf pancreas lipase (PPL), *Candida antarctica* lipase B on immobead 150 immobilizer (CA). (Uwe Theo Bornscheuer, Romas Joseph Kazlauskas: Hydrolases in Organic Synthesis: Regio- and Stereoselective Biotransformation, 2nd Edition 2005, John Wiley and Sons, ISBN: 978-3-527-31029-6).

Of the commercially available enzyme preparations numerous may be applied, as for example:
L1754 Sigma
Lipase from *Candida rugosa*
Type VII, ≥700 unit/mg solid
Synonym: Triacylglycerol acylhydrolase, Triacylglycerol lipase
Lipase, immobilized on Immobead 150 from *Candida rugosa*
Lipase from *Candida antarctica* (≥1.0 U/mg, lyophilized, powder, beige, 0.3 U/mg)
Lipase from *Rhizomucor miehei*
≥20,000 U/g
Synonym: Palatase® 20,000 L
62309 Sigma
Lipase from *Pseudomonas cepacia*
powder, light beige, ≥30 U/mg
Synonym: PS Lipase, Triacylglycerol acylhydrolase, Triacylglycerol lipase
743941 Aldrich
Lipase A, *Candida antarctica*, CLEA
≥1500 U/mL
Synonym: Lipase A, *Candida antarctica*
Lipase from *Pseudomonas fluorescens*
powder, slightly beige, ≥160 U/mg
Lipase B *Candida antarctica* immobilized on immobead
Lipases are suitable to form or hydrolyze ester bonds and transform compounds containing ester bonds into each other, i.e. suitable for trans-esterification. They always take part in the reactions as catalysts.

From the viewpoint of our present invention the most important characteristic of lipases is that they react with the isomers of the optically active carboxylic acid derivatives at highly different rates, especially, if the chiral centre is situated next to the carbonyl carbon. Owing to this characteristic, they may be used for the resolution of optically active compounds.

The above ability is shown in the following Figure:

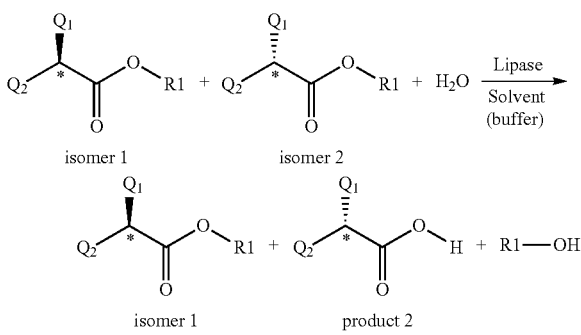

Ester formation and acylation may be carried out by methods known to those skilled in the art.

According to a preferred embodiment of the invention phosphonic acid esters of formulae (1) and (1') may be prepared by a method not described before in the literature.

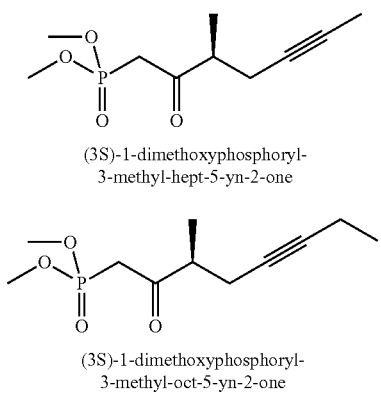

(3S)-1-dimethoxyphosphoryl-3-methyl-hept-5-yn-2-one (3S)-1-dimethoxyphosphoryl-3-methyl-oct-5-yn-2-one Reaction steps of the process are show in the Figure below:

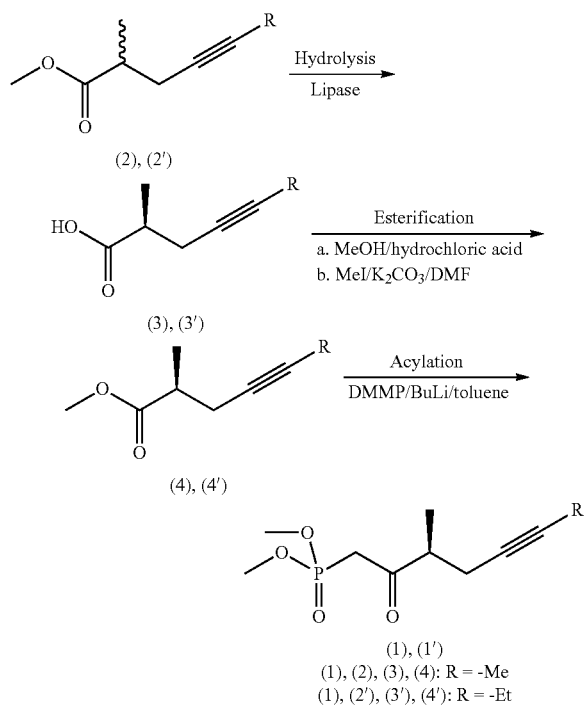

(1), (2), (3), (4): R = -Me
(1'), (2'), (3'), (4'): R = -Et

Novelty of the process is that the first, hydrolysis step is carried out enzymatically and owing to this, the racemic starting materials result a product which is considerably enriched in the desired isomer, i.e. we carry out kinetic resolution. Optical purity of the product may further increase on repeating the hydrolysis and esterification steps. Using *Candida rugosa* lipase the racemic methyl 2-methylhex-4-ynoate (2) after the first hydrolysis results the acid (3) in 70% enantiomeric purity. Following esterification and repeated hydrolysis the enantiomeric purity increases to 90-95%, and after further esterification and hydrolysis the (S)-2-methyl-4-hexynoic acid (3) is gained in 97-99% enantiomeric purity.

In the followings we describe preferred reaction conditions of the individual steps: Hydrolysis: The racemic staring material (2) is dissolved in methyl tert.-butyl ether. To the solution water, and then lipase enzyme are added and the reaction mixture is agitated at 20-40° C. till the end of the reaction. Depending on the amount and activity of the enzyme, the reaction time is 2-48 hours. During the reaction the pH is maintained between 4-7. At the end of the reaction the product is extracted with methyl tert.-butyl ether. The product solution is washed with saturated sodium chloride solution, dried over sodium sulfate, and by evaporation the product (3) is obtained. Yield 38-50%.

As starting material, instead of the methyl ester, ethyl, propyl, isopropyl and butyl esters may also be applied. We applied mainly *Candida rugosa* lipase enzyme for the reaction. As solvent, n-hexane, toluene and diisopropyl ether may also be used instead of methyl tert.-butyl ether. In the course of the repeated hydrolyses the yield increases: the yield of the second hydrolysis is 70-80%, that of the third is 80-90%.

Esterification: Esterification may be carried out by a variety of methods, here we describe two methods as examples:

a) The acid (3) is dissolved in methanol, a small amount of concentrated hydrochloric acid is added to it and the mixture is agitated at 20-30° C. till the end of the reaction. Following concentration by evaporation, the reaction mixture is poured onto salt solution, the product (4) is extracted with toluene or with methyl tert.-butyl ether, washed with salt solution, dried over sodium sulfate and evaporated. Yield: 70-80%.

b) The acid (3) is dissolved in dimethylformamide and in the presence of potassium carbonate esterified with methyl iodide at 25-35° C. At the end of the reaction the product (4) is extracted with methyl tert.-butyl ether: n-hexane mixture. The extract is washed with salt solution, dried over sodium sulfate and evaporated. Yield: 90-97%.

Acylation: To the solution of butyl lithium first the toluene solution of dimethyl methylphosphonate (DMMP) is added dropwise at −75-(−85)° C., then to resulting solution the ester (4) dissolved in toluene is added dropwise at −75-(−85)° C. At the end of the acylation reaction the reaction mixture is poured onto acid solution and the product (1) is extracted with toluene or ethyl acetate. The extract is washed with salt solution, dried over sodium sulfate and evaporated. Yield: 90-95%.

Product (1') is prepared in exactly the same way.

Optical purity of the products was determined by chiral high pressure liquid chromatography (HPLC) method applying chiral column.

(S)-dimethoxyphosphoryl-3-methyl-hept-5-yn-2-one:
Instrument: Isocratic HPLC system with Photodiode array detector,
Electronic data processing system and Automatic sample management system
Column: Chiralpak AD-H, 250×4.6 mm, 5 μm
Mobile phase: Hexane:ethanol=9:1
Detection wavelength: 290 nm
Flow rate: 1.0 ml/minute
Injected volume: 10 μl
Column temperature: 25° C.
Sample temperature: 25° C.
Run time: 30 minute
Sample dissolution: eluent (S)-2-methyl-4-hexynoic acid Column: Zorbax RX SIL 250×4.6 mm 5 μm
Eluent: Hexane: isopropanol=88:12

Flow rate: 1.0 ml/minute
Column temperature: 30° C.
Detection: 220 nm
Injected volume: 10 μl
Run time: 25 min
Sample dissolution: TBME
  Preparation of the derivatisation solutions:
  1. 100 mg of CDI* is dissolved in 1 ml of acetonitrile.
  2. 150 mg of (R)-FEa* is dissolved in 1 ml of ACN.
  *CDI=1,1'-carbonyl-diimidazole, (R)-FEa=(R)-1-phenyl-ethylamine Details of our process are demonstrated in the examples, without limiting the invention to the examples.

EXAMPLES

1.) Preparation of (S)-2-Methyl-4-Hexynoic Acid

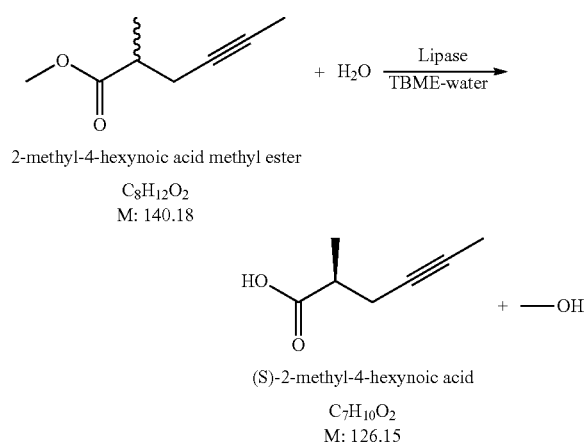

2-methyl-4-hexynoic acid methyl ester
$C_8H_{12}O_2$
M: 140.18

(S)-2-methyl-4-hexynoic acid
$C_7H_{10}O_2$
M: 126.15

841 g of racemic 2-methyl-4-hexynoic acid methyl ester is dissolved in 8.4 L of methyl tert-butyl ether, 30 L demi water and 126 g of *Candida rugosa* lipase (activity: 1200 U/mg) are added. The reaction mixture is agitated at 25-30° C. until approx. 45% conversion is reached, while the pH is adjusted to around 6 by addition of 1 M NaHCO$_3$ solution. At the end of the reaction 1 M NaHCO$_3$ solution is added, the phases are separated, the aqueous phase is washed twice with methyl tert-butyl ether, then 1 M NaHSO$_4$ solution is added and the mixture is extracted with methyl tert-butyl ether. The united aqueous phase is washed with saturated NaCl solution, dried over sodium sulfate. The drying material is filtered off, the filtrate solution which contains the product is evaporated.

Yield: 366.06 g (48.4%) (S)-2-methyl-4-hexynoic acid, enantiomeric purity: 70.2%.

2.) Preparation of (S)-2-Methyl-4-Hexynoic Acid Methyl Ester

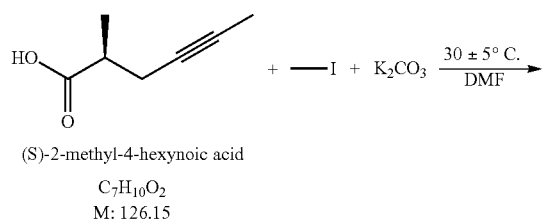

(S)-2-methyl-4-hexynoic acid
$C_7H_{10}O_2$
M: 126.15

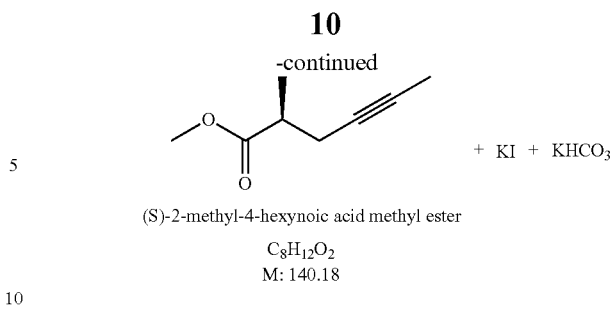

(S)-2-methyl-4-hexynoic acid methyl ester
$C_8H_{12}O_2$
M: 140.18

347 g of (S)-2-methyl-4-hexynoic acid (enantiomeric purity 70.2%) is dissolved in 2 L of dimethylformamide, 536 g of water-free potassium carbonate, and 457 ml of methyl iodide are added. The reaction mixture is agitated at 25-35° C. while esterification proceeds, then it is destroyed by addition of water and 1 M NaHSO$_4$ solution. The aqueous phase is extracted with methyl tert-butyl ether:n-hexane mixture, the united organic phase is washed with saturated salt solution, dried over sodium sulfate. The drying material is filtered off, the liquid filtrate is evaporated.

Yield: 369.93 g (96.0%) (S)-2-Methyl-4-hexynoic acid methyl ester, enantiomeric purity: 70.2%.

3.) Preparation of (S)-2-Methyl-4-Hexynoic Acid 369.9 g (S)-2-Methyl-4-hexynoic acid methyl ester (enantiomeric purity: 70.2%) is dissolved in 3.7 L of methyl tert-butyl ether, 13.2 L demi water and 55 g of *Candida rugosa* lipase (activity: 1200 U/mg) are added. The reaction mixture is agitated at 25-30° C. until reaching approx. 80% conversion, while adjusting the pH around 6 by addition of 1 M NaHCO$_3$ solution. At the end of the reaction 1 M NaHCO$_3$ solution is added, the phases are separated, the aqueous phase is washed twice with methyl tert-butyl ether, then 1 M NaHSO$_4$ solution is added and the mixture is extracted with methyl tert-butyl ether. The united aqueous phase is washed with saturated NaCl solution, dried over sodium sulfate. The drying material is filtered off, the filtrate solution which contains the product is evaporated.

Yield: 255.80 g (76.8%) (S)-2-Methyl-4-hexynoic acid, enantiomeric purity: 93.0%.

4.) Preparation of (S)-2-Methyl-4-Hexynoic Acid Methyl Ester 252 g (S)-2-methyl-4-hexynoic acid (enantiomeric purity 93.0%) is dissolved in 1.47 L of dimethylformamide, 390 g of water-free potassium carbonate and 332 ml of methyl iodide are added. The reaction mixture is agitated at 25-35° C. while esterification proceeds, then it is destroyed by addition of water and 1 M NaHSO$_4$ solution. The aqueous phase is extracted with methyl tert-butyl ether:n-hexane mixture, the united organic phase is washed with saturated salt solution and dried over sodium sulfate. The drying material is filtered off, the liquid filtrate is evaporated.

Yield: 272.28 g (97.1%) (S)-2-Methyl-4-hexynoic acid methyl ester, enantiomeric purity: 93.0%.

5.) Preparation of (S)-2-Methyl-4-Hexynoic Acid 272.3 g (S)-2-Methyl-4-hexynoic acid methyl ester (enantiomeric purity: 93.0%) is dissolved in 2.7 L of methyl tert-butyl ether, 9.7 L demi water and 41 g of *Candida rugosa* lipase (activity: 1200 U/mg) are added. The reaction mixture is agitated at 25-30° C. until reaching approx. 90% conversion, while adjusting the pH around 6 by addition of 1 M NaHCO$_3$ solution. At the end of the reaction 1 M NaHCO$_3$ solution is added, the phases are separated, the aqueous phase is washed twice with methyl tert-butyl ether, then 1 M NaHSO$_4$ solution is added and the mixture is extracted with methyl tert-butyl ether. The united aqueous phase is washed with saturated NaCl solution, dried over sodium sulfate. The drying material is filtered off, the filtrate solution which contains the product is evaporated.

Yield: 209.16 g (85.4%) (S)-2-methyl-4-hexynoic acid, enantiomeric purity: 97.6%.

6.) Preparation of (S)-2-Methyl-4-Hexynoic Acid Methyl Ester 200 g of (S)-2-methyl-4-hexynoic acid (enantiomeric purity 97.6%) is dissolved in 1.2 L of dimethylformamide, 309 g of water-free potassium carbonate and 264 ml of methyl iodide are added. The reaction mixture is agitated at 25-35° C. while esterification proceeds, then it is destroyed by addition of water and 1 M NaHSO$_4$ solution. The aqueous phase is extracted with methyl tert-butyl ether:n-hexane mixture, the united organic phase is washed with saturated salt solution, dried over sodium sulfate. The drying material is filtered off, the liquid filtrate is evaporated.

Yield: 200.32 g (90.2%) (S)-2-Methyl-4-hexynoic acid methyl ester, enantiomeric purity: 97.6%.

7.) Preparation of (S)-Dimethoxyphosphoryl-3-methyl-hex-5-yn-one

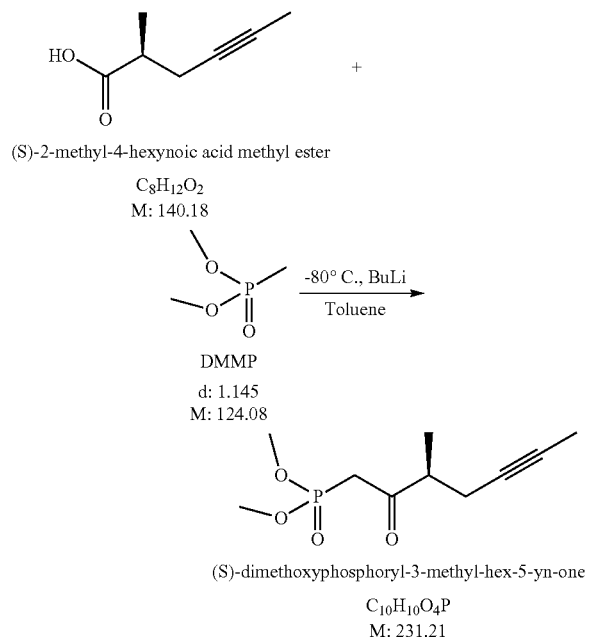

To 1.3 L of distilled toluene, under nitrogen atmosphere, 666 ml of 1.6 M butyl lithium solution is added and the mixture is cooled to −80±5° C. While keeping that temperature, the solution of 123 ml of dimethyl methylphosphonate in 495 ml of distilled toluene is added. After 15 minutes of agitation the solution of 82 g (S)-2-methyl-4-hexynoic acid methyl ester (enantiomeric purity 97.6%) in 405 ml of distilled toluene is added at −80±5° C. The reaction mixture is agitated at that temperature for another 30 minutes. After proceeding of the acylation reaction the mixture is poured onto acid solution. The phases are separated, the aqueous phase is extracted with ethyl acetate, the united organic phase is washed with saturated salt solution and evaporated.

The crude product is purified by gravity chromatography using gradient mixtures of n-hexane: ethyl acetate.

Yield: 127.45 g (94.0%) (S)-Dimethoxyphosphoryl-3-methyl-hex-5-yn-one, enantiomeric purity: 97.8%.

8.) Preparation of (S)-2-Methyl-4-Heptynoic Acid

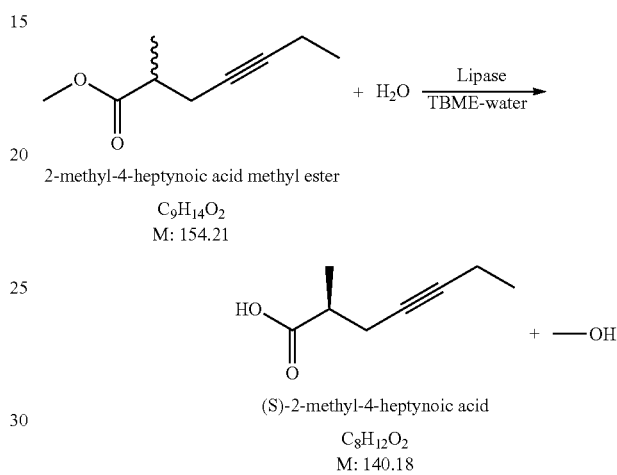

4.270 g of racemic 2-methyl-4-heptynoic acid methyl ester is dissolved in 43 ml of methyl tert-butyl ether, 152 ml of demi water and 0.534 g of *Candida rugosa* lipase (activity: 1300 U/mg) are added. The reaction mixture is agitated at 25-30° C. until reaching approx. 45% conversion, while adjusting the pH around 6 by addition of 1 M NaHCO$_3$ solution. At the end of the reaction 1 M NaHCO$_3$ solution is added, the phases are separated, the aqueous phase is washed twice with methyl tert-butyl ether, then 1 M NaHSO$_4$ solution is added and the mixture is extracted with methyl tert-butyl ether. The united aqueous phase is washed with saturated NaCl solution, dried over sodium sulfate. The drying material is filtered off, the filtrate solution which contains the product is evaporated.

Yield: 1.499 g (38.6%) (S)-2-Methyl-4-heptynoic acid, enantiomeric purity: 68.6%.

9.) Preparation of (S)-2-Methyl-4-Heptynoic Acid Methyl Ester

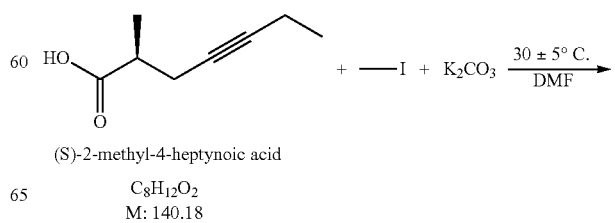

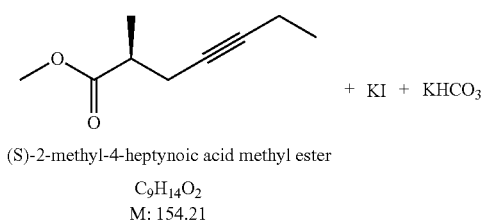

(S)-2-methyl-4-heptynoic acid methyl ester
C₉H₁₄O₂
M: 154.21

+ KI + KHCO₃

1.460 g (S)-2-methyl-4-heptynoic acid (enantiomeric purity 68.6%) is dissolved in 8 ml of dimethylformamide, 2.030 g of water-free potassium carbonate and 1.7 ml of methyl iodide are added. The reaction mixture is agitated at 25-35° C. till esterification proceeds, then it is destroyed by addition of water and 1 M NaHSO₄ solution. The aqueous phase is extracted with methyl tert-butyl ether:n-hexane mixture, the united organic phase is washed with saturated salt solution, dried over sodium sulfate. The drying material is filtered off, the liquid filtrate is evaporated.

Yield: 1.366 g (85.1%) (S)-2-methyl-4-heptynoic acid methyl ester, enantiomeric purity: 68.6%.

10.) Preparation of (S)-2-Methyl-4-Heptynoic Acid 1.366 g of (S)-2-methyl-4-heptynoic acid methyl ester (enantiomeric purity: 68.6%) is dissolved in 14 ml of methyl tert-butyl ether, 49 ml demi water and 0.171 g of *Candida rugosa* lipase (activity: 1300 U/mg) are added. The reaction mixture is agitated at 25-30° C. until reaching approx. 45% conversion, while adjusting the pH around 6 by addition of 1 M NaHCO₃ solution. At the end of the reaction 1 M NaHCO₃ solution is added, the phases are separated, the aqueous phase is washed twice with methyl tert-butyl ether, then 1 M NaHSO₄ solution is added and the mixture is extracted with methyl tert-butyl ether. The united aqueous phase is washed with saturated NaCl solution, dried over sodium sulfate. The drying material is filtered off, the filtrate solution which contains the product is evaporated.

Yield: 0.646 g (52.0%) (S)-2-Methyl-4-heptynoic acid, enantiomeric purity: 91.0%.

11.) Preparation of (S)-2-Methyl-4-Heptynoic Acid Methyl Ester 0.592 g of (S)-2-methyl-4-heptynoic acid (enantiomeric purity 91.0%) is dissolved in 3.0 ml of dimethylformamide, 0.820 g of water-free potassium carbonate and 0.70 ml of methyl iodide are added. The reaction mixture is agitated at 25-35° C. while esterification proceeds, then it is destroyed by addition of water and 1 M NaHSO₄ solution. The aqueous phase is extracted with methyl tert-butyl ether:n-hexane mixture, the united organic phase is washed with saturated salt solution, dried over sodium sulfate. The drying material is filtered off, the liquid filtrate is evaporated.

Yield: 0.569 g (87.4%) (S)-2-methyl-4-heptynoic acid methyl ester, enantiomeric purity: 91.0%.

12.) Preparation of (S)-Dimethoxyphosphoryl-3-methyl-hept-5-yn-one

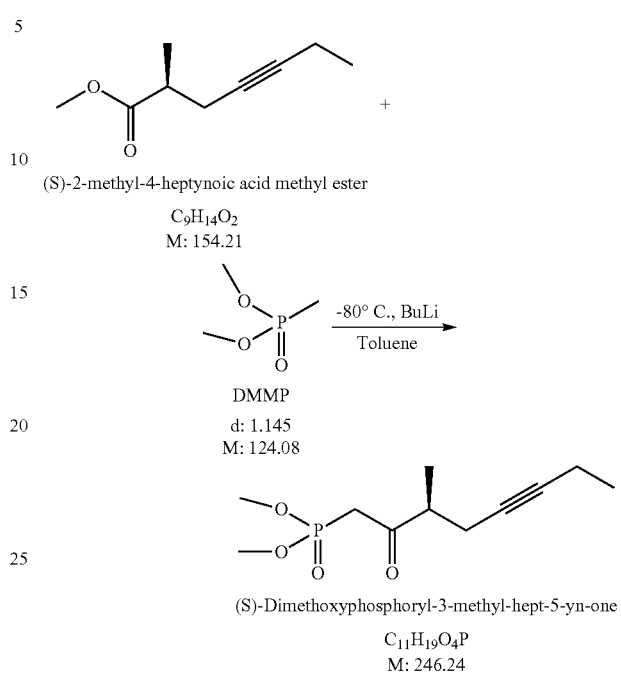

To 17 ml of distilled toluene, under nitrogen atmosphere, 8.1 ml of 1.6 M butyl lithium solution is added and the mixture is cooled to −80±5° C. While keeping that temperature, the solution of 1.5 ml of dimethyl methylphosphonate in 3.3 ml of distilled toluene is added. After 15 minutes of agitation the solution of 0.549 g of (S)-2-methyl-4-heptynoic acid methyl ester (enantiomeric purity 91.0%) in 3.0 ml of distilled toluene is added at −80±5° C. The reaction mixture is agitated at that temperature for another 30 minutes. After proceeding of the acylation reaction the mixture is poured onto acid solution. The phases are separated, the aqueous phase is extracted with ethyl acetate, the united organic phase is washed with saturated salt solution and evaporated.

The crude product is purified by gravity chromatography using gradient mixtures of n-hexane: ethyl acetate Yield: 0.782 g (89.2%) (S)-Dimethoxyphosphoryl-3-methyl-hept-5-yn-one, enantiomeric purity: 96.7%.

The invention claimed is:

1. Process for the preparation of chiral carboxylic acids of general formula (I),

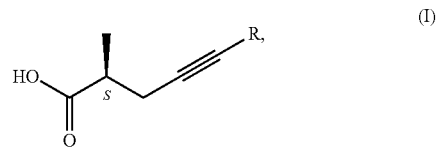

where R is H or methyl group, wherein a racemic carboxylic acid ester of general formula (II),

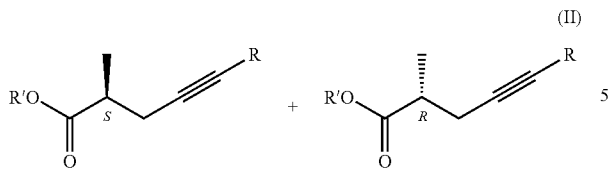

(II)

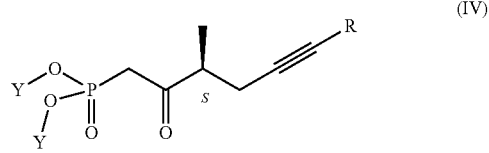

(III)

where R' is Me, Et, Pr, i-Pr, Bu, and
R is as defined above,
is enzymatically hydrolysed using a hydrolase enzyme, thereby obtaining the chiral carboxylic acid of general formula (I).

2. The process as defined in claim 1, wherein as hydrolase enzyme *Candida rugosa* lipase enzyme is applied.

3. The process as defined in claim 1, wherein the hydrolysis is carried out in the presence of a solvent.

4. The process as defined in claim 3, wherein the solvent is selected from the group of ethers, hydrocarbon-type and aromatic solvents, and mixtures thereof.

5. The process as defined in claim 4, wherein as solvent methyl tert-butyl ether is applied.

6. The process as defined in claim 1, wherein depending on the amount and activity of the enzyme, the reaction time is 2-48 hours.

7. The process as defined in claim 1, wherein the reaction is performed at 20-40° C.

8. The process as defined in claim 2, wherein depending on the amount and activity of the enzyme, the reaction time is 2-48 hours.

9. The process as defined in claim 3, wherein depending on the amount and activity of the enzyme, the reaction time is 2-48 hours.

10. The process as defined in claim 4, wherein depending on the amount and activity of the enzyme, the reaction time is 2-48 hours.

11. The process as defined in claim 2, wherein the reaction is performed at 20-40° C.

12. The process as defined in claim 3, wherein the solvent is selected from the group of diisopropyl ether, methyl tert-butyl ether, n-hexane, toluene, and mixtures thereof.

13. The process as defined in claim 1, where in a subsequent step, the chiral acid of general formula (I) is converted into a salt with a metal ion, protonated ammonia, or an amine.

14. The process as defined in claim 1, further comprising a subsequent step (a), wherein the chiral acid of general formula (I) is converted into a chiral ester of general formula (III)

where R' and R are as defined in claim 1, and optionally, in a subsequent step (b)

the chiral ester of general formula (III) obtained in step (a) is converted into a chiral compound of general formula (IV),

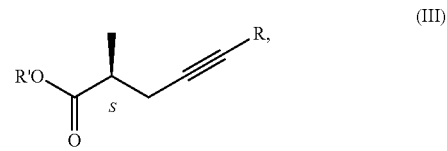

(IV)

where Y is Me or Et and R is as defined in claim 1.

15. The process as defined in claim 14, wherein the chiral ester of general formula (III) obtained in step (a) is enzymatically hydrolysed by the process of claim 1, to obtain the chiral carboxylic acid of general formula (I) with increased enantiomeric purity, and optionally, the esterification process of said step (a) and the hydrolysis process of claim 1 are repeated, to obtain the chiral carboxylic acid of general formula (I) with further increased enantiomeric purity.

16. The process as defined in claim 5, wherein depending on the amount and activity of the enzyme, the reaction time is 2-48 hours.

17. The process as defined in claim 3, wherein the reaction is performed at 20-40° C.

18. The process as defined in claim 4, wherein the reaction is performed at 20-40° C.

19. The process as defined in claim 5, wherein the reaction is performed at 20-40° C.

20. The process as defined in claim 6, wherein the reaction is performed at 20-40° C.

* * * * *